United States Patent
Chang et al.

(10) Patent No.: US 11,363,968 B2
(45) Date of Patent: Jun. 21, 2022

(54) CENTER OF PRESSURE BASED CONTROL SYSTEM AND METHOD

(71) Applicant: Chang Gung University, Taoyuan (TW)

(72) Inventors: Ya-Ju Chang, Taipei (TW); Jiunn-Woei Liaw, Taipei (TW); Hung-Bin Chen, Taipei (TW)

(73) Assignee: Chang Gung University, Taoyuan (TW)

(*) Notice: Subject to any disclaimer, the term of this patent is extended or adjusted under 35 U.S.C. 154(b) by 596 days.

(21) Appl. No.: 15/837,872

(22) Filed: Dec. 11, 2017

(65) Prior Publication Data
US 2018/0160941 A1   Jun. 14, 2018

(30) Foreign Application Priority Data

Dec. 12, 2016 (TW) .................. 105141002

(51) Int. Cl.
*A61B 5/11*    (2006.01)
*A61B 5/103*   (2006.01)
*A61B 5/00*    (2006.01)

(52) U.S. Cl.
CPC .......... *A61B 5/1116* (2013.01); *A61B 5/1036* (2013.01); *A61B 5/6887* (2013.01);
(Continued)

(58) Field of Classification Search
CPC ............................................. A61B 2562/0252
(Continued)

(56) References Cited

U.S. PATENT DOCUMENTS 4,267,728 A * 5/1981 Manley ................ A43B 3/0005
                                                  345/629
5,388,591 A * 2/1995 De Luca .............. A61B 5/1036
                                                  600/592
(Continued)

FOREIGN PATENT DOCUMENTS

CN         103052455 A      4/2013

OTHER PUBLICATIONS

Delbressine F, Timmermans A, Beursgens L, et al. Motivating arm-hand use for stroke patients by serious games. Conf Proc IEEE Eng Med Biol Soc. 2012;2012:3564-3567. doi:10.1109/EMBC.2012.6346736 (Year: 2012).*

(Continued)

*Primary Examiner* — Sean P Dougherty
(74) *Attorney, Agent, or Firm* — Osha Bergman Watanabe & Burton LLP

(57) ABSTRACT

A center of pressure (CoP) based control system includes a sensing device and an electronic device connected to the sensing device. The sensing device includes sensors each of which continuously measures force exerted thereon by a subject and generates a sense signal based on a result of the measurement. The electronic device is connected to the sensing device, and receives the sense signals from the respective sensors, generates CoP data associated with a CoP trajectory based on the sense signals, determines whether a turning point exists in the CoP trajectory, generates an indication signal based on a result of the determination, and generates a control signal based on a direction of one of displacements of the CoP.

12 Claims, 4 Drawing Sheets

(52) U.S. Cl.
CPC ... *A61B 2505/09* (2013.01); *A61B 2562/0247* (2013.01); *A61B 2562/04* (2013.01)

(58) Field of Classification Search
USPC .................................................. 600/592
See application file for complete search history.

(56) References Cited

U.S. PATENT DOCUMENTS

| | | | | |
|---|---|---|---|---|
| 6,624,802 | B1* | 9/2003 | Klein | A63F 13/06 |
| | | | | 345/156 |
| 8,764,532 | B1* | 7/2014 | Berme | A61B 5/742 |
| | | | | 463/7 |
| 8,974,402 | B2* | 3/2015 | Oddsson | A61B 5/1121 |
| | | | | 600/595 |
| 9,149,222 | B1* | 10/2015 | Zets | A61B 5/1116 |
| 9,943,250 | B2* | 4/2018 | Plotnik-Peleg | A61B 5/744 |
| 2005/0131317 | A1* | 6/2005 | Oddsson | A61B 5/1036 |
| | | | | 600/592 |
| 2006/0293613 | A1* | 12/2006 | Fatehi | A61B 5/1036 |
| | | | | 600/587 |
| 2008/0280740 | A1* | 11/2008 | Knecht | A63B 22/18 |
| | | | | 482/146 |
| 2011/0282245 | A1* | 11/2011 | Decker | A61B 5/1071 |
| | | | | 600/587 |
| 2012/0071300 | A1* | 3/2012 | Shapiro | F41A 33/00 |
| | | | | 482/54 |
| 2012/0253234 | A1* | 10/2012 | Yang | A61B 5/1038 |
| | | | | 600/595 |
| 2013/0218053 | A1* | 8/2013 | Kaiser | A61B 5/7267 |
| | | | | 600/595 |
| 2013/0226039 | A1* | 8/2013 | Shani | A61B 5/1128 |
| | | | | 600/595 |
| 2013/0244211 | A1* | 9/2013 | Dowling | G06F 19/3481 |
| | | | | 434/247 |
| 2013/0281888 | A1* | 10/2013 | Bender | G09B 19/00 |
| | | | | 600/595 |
| 2014/0081177 | A1* | 3/2014 | Eguibar | A61B 5/1036 |
| | | | | 600/595 |
| 2014/0276130 | A1* | 9/2014 | Mirelman | A61B 5/744 |
| | | | | 600/483 |
| 2015/0238816 | A1* | 8/2015 | Naderer | A61B 5/0037 |
| | | | | 482/4 |
| 2016/0007904 | A1* | 1/2016 | Vardy | A61B 5/0022 |
| | | | | 600/476 |
| 2017/0229041 | A1* | 8/2017 | Reichow | A63B 69/00 |

OTHER PUBLICATIONS

Mellone, S., Mancini, M., King, L. A., Horak, F. B., Chiari, L. (2016). The quality of turning in Parkinson's disease: A compensatory strategy to prevent postural instability? Journal of NeuroEngineering and Rehabilitation, 13(1). doi:10.1186/s12984-016-0147-4 (Year: 2016).*
Cirstea, M., & Levin, M. (2007). Improvement of Arm Movement Patterns and Endpoint Control Depends on Type of Feedback During Practice in Stroke Survivors. Neurorehabilitation and Neural Repair, 21(5), 398-411. doi:10.1177/1545968306298414 (Year: 2007).*
Borges, C. M. (2012). Compensatory Movement Detection Through Inertial Sensor Positioning for Post-Stroke Rehabilitation. Proceedings of the International Conference on Bio-inspired Systems and Signal Processing. doi:10.5220/0003798102970302 (Year: 2012).*
Subramanian, S., Knaut, L., Beaudoin, C., Mcfadyen, B., Feldman, A., & Levin, M. (2006). Virtual Reality Environments for Rehabilitation of the Upper Limb after Stroke. 2006 International Workshop on Virtual Rehabilitation. doi:10.1109/iwvr.2006.1707520 (Year: 2006).*
Sevšek, France. (2006). Determination of sway area by Fourier analysis of its contour. 514-518. (Year: 2006).*
King, L., St George, R., Carlson-Kuhta, P., Nutt, J. and Horak, F., 2010. Preparation for Compensatory Forward Stepping in Parkinson's Disease. Archives of Physical Medicine and Rehabilitation, 91(9), pp. 1332-1338. (Year: 2010).*
Search Report appended to an Office Action, which was issued to Taiwanese counterpart application No. 105141002 by the TIPO dated Nov. 14, 2017, with an English translation thereof (2 pages).

* cited by examiner

CENTER OF PRESSURE BASED CONTROL SYSTEM AND METHOD

CROSS-REFERENCE TO RELATED APPLICATION

This application claims priority of Taiwanese Patent Application No. 105141002, filed on Dec. 12, 2016.

FIELD

The disclosure relates to a control system and a control method, and more particularly to a center of pressure (CoP) based control system and a CoP based control method.

BACKGROUND

A conventional rehabilitation device lacks the functionality of determining whether compensatory movements, such as leg swings, body tilts, shrugs, foot circling and the like, are utilized by a subject undergoing balance control training, so an effect of rehabilitation of individuals with balance impairment is adversely affected. Moreover, since a subject in a process of rehabilitation is often requested to perform repetitive body movements which may lead to boredom and tiresomeness, the subject is prone to being fatigued and losing concentration.

SUMMARY

Therefore, an object of the disclosure is to provide a center of pressure (Cop) based control system and two CoP based control methods that can alleviate at least one of the drawbacks of the prior art.

According to one aspect of the disclosure, the CoP based control system includes a sensing device and an electronic device.

The sensing device includes a plurality of sensors each of which is configured to make continuous measurement of force exerted thereon by a subject and to generate a sense signal based on a result of the measurement.

The electronic device is electrically connected to the sensing device, and is configured to receive the sense signals from the respective sensors, to generate, based on the sense signals received from the respective sensors, CoP data associated with a CoP trajectory which indicates displacements of a CoP of the subject, to make a determination as to whether a turning point exists in the CoP trajectory so as to determine whether anticipatory postural adjustment (APA) exists in the subject, to generate an indication signal which indicates whether or not APA exists in the subject based on a result of the determination, and to generate a control signal based on a direction of one of the displacements of the CoP, wherein the determination as to whether a turning point exists in the CoP trajectory is made based on at least one of an included angle between any adjacent two of the displacements of the CoP, a magnitude of one of the displacements of the CoP preceding a possible turning point on the CoP trajectory, or a ratio between magnitudes of two of the displacements of the CoP respectively preceding and succeeding the possible turning point.

According to another aspect of the disclosure, the CoP based control method is to be implemented by the CoP based control system mentioned above, and includes the following steps of:

by each of a plurality of sensors of the CoP based control system, making continuous measurement of force exerted thereon by a subject and generating a sense signal based on a result of the measurement;

by an electronic device of the CoP based control system, receiving the sense signals from the respective sensors;

by the electronic device of the CoP based control system, generating, based on the sense signals received from the respective sensing units, CoP data associated with a CoP trajectory which indicates displacements of a CoP of the subject;

by the electronic device of the CoP based control system, making a determination as to whether a turning point exists in the CoP trajectory so as to determine whether APA exists in the subject;

by the electronic device of the CoP based control system, generating an indication signal which indicates whether or not the APA exists in the subject based on a result of the determination; and by the electronic device of the CoP based control system, generating a control signal based on a direction of one of the displacements of the CoP;

wherein the determination as to whether a turning point exists in the CoP trajectory is made based on at least one of an included angle between any adjacent two of the displacements of the CoP, a magnitude of one of the displacements of the CoP preceding a possible turning point on the CoP trajectory, or a ratio between magnitudes of two of the displacements of the CoP respectively preceding and succeeding the possible turning point.

According to further another aspect of the disclosure, the CoP based control method is to be implemented by the CoP based control system mentioned above, and includes the following steps of:

by each of a plurality of sensors of the CoP based control system, making continuous measurement of force exerted thereon by a subject and generating a sense signal based on a result of the measurement;

by an electronic device of the CoP based control system, receiving the sense signals from the respective sensors;

by the electronic device of the CoP based control system, generating, based on the sense signals received from the respective sensing units, CoP data associated with a CoP trajectory which indicates displacements of a CoP of the subject;

by the electronic device of the CoP based control system, making a determination as to whether a turning point exists in the CoP trajectory so as to determine whether a compensatory movement exists in the subject;

by the electronic device of the CoP based control system, generating an indication signal which indicates whether or not the a compensatory movement exists in the subject based on a result of the determination; and by the electronic device of the CoP based control system, generating a control signal based on a direction of one of the displacements of the CoP.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
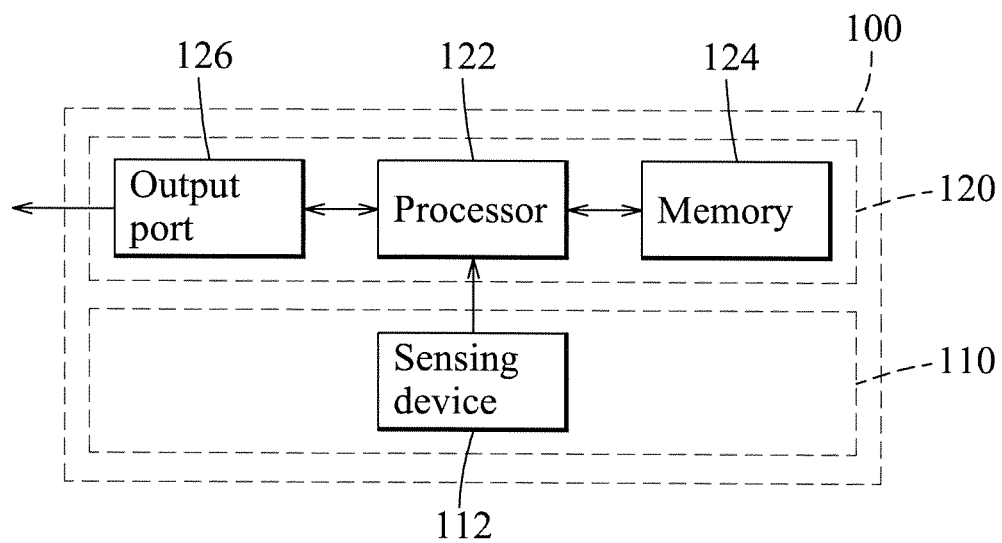
FIG. 1 is a schematic diagram illustrating an embodiment of a center of pressure (CoP) based control system according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Referring to FIG. 1, an embodiment of a center of pressure (CoP) based control system 100 is illustrated. The CoP based control system 100 includes a sensing device 112 and an electronic device 120 electrically connected to the sensing device 112. The connection between the sensing device 112 and the electronic device 120 may be implemented by one of a wired connection and a wireless connection, either one of which is well known to one skilled in the relevant art, so a detailed explanation of the same is omitted herein for the sake of brevity.

The electronic device 120 includes a processor 122, an output port 126 and a memory 124. The processor 122 is communicable with the output port 126 and the memory 124. In one embodiment, the electronic device 120 may be implemented as a notebook computer, a tablet computer, a smartphone, or a customized circuit that is configurable/programmable in a software manner and/or hardware manner to implement functionalities of this disclosure. However, the implementation of the electronic device 120 is not limited to what are disclosed herein.

Figure 2:
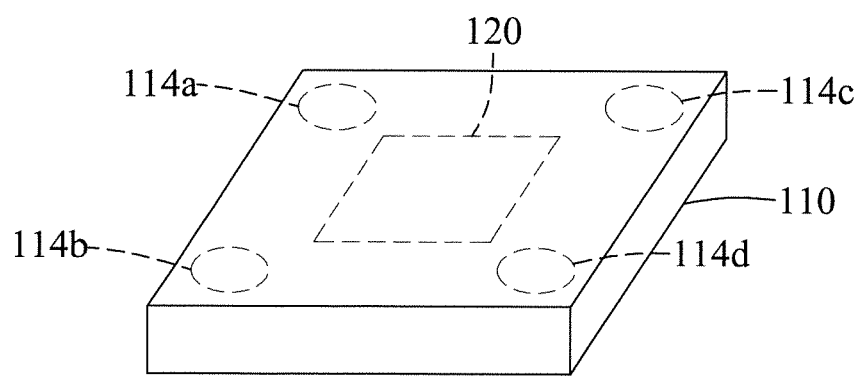
FIG. 2 is a perspective diagram illustrating an embodiment of disposition of sensors of the CoP based control system on a platform for supporting the subject.
Figure 5:
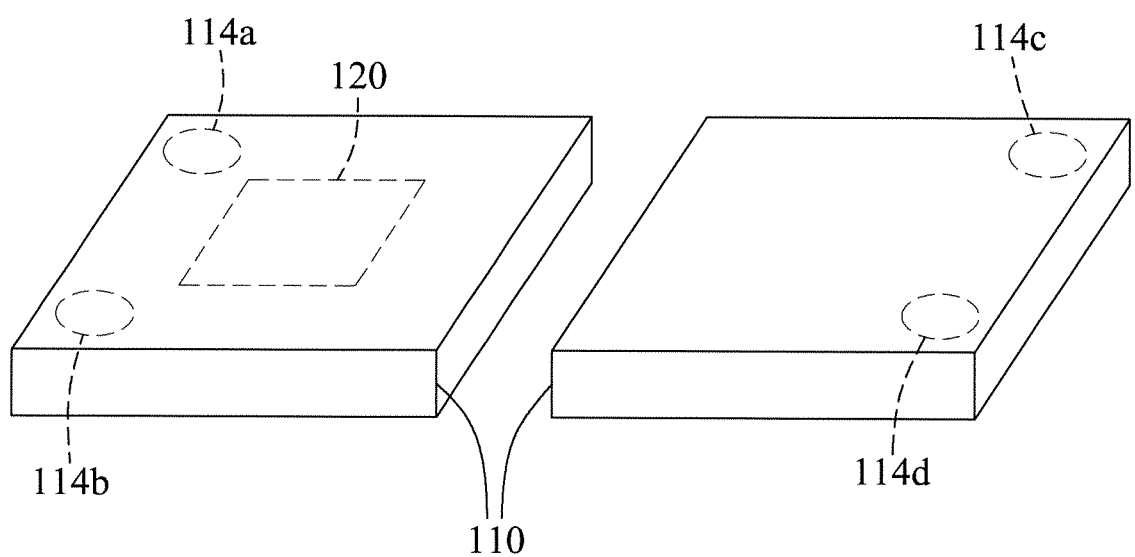
FIG. 5 is a perspective diagram illustrating another embodiment of disposition of the sensors of the CoP based control system on two platforms for supporting the subject.

Referring to FIG. 2, the electronic device 120 is disposed in a platform 110, but in other embodiments, the electronic device 120 may be disposed outside the platform 110. In addition, the sensing device 112 includes a plurality of sensors (114a-114d) each of which is configured to make continuous measurement of force exerted thereon by a subject and to generate a sense signal based on a result of the measurement. It is worth to note that in this embodiment, the sensors (114a-114d) are disposed in the platform 110 used for supporting the subject, but implementation of the placement of the sensors (114a-114d) is not limited thereto. In one embodiment, the sensors (114a-114d) are disposed on two platforms (e.g., a pair of shoes) used for supporting the subject as shown in FIG. 5. In one embodiment, each of the sensors (114a-114d) may be implemented by a piezoelectric plate, a strain gauge, a load cell, a magnetometer, or any device configured to implement the aforementioned functions in a similar manner.

Figure 3:
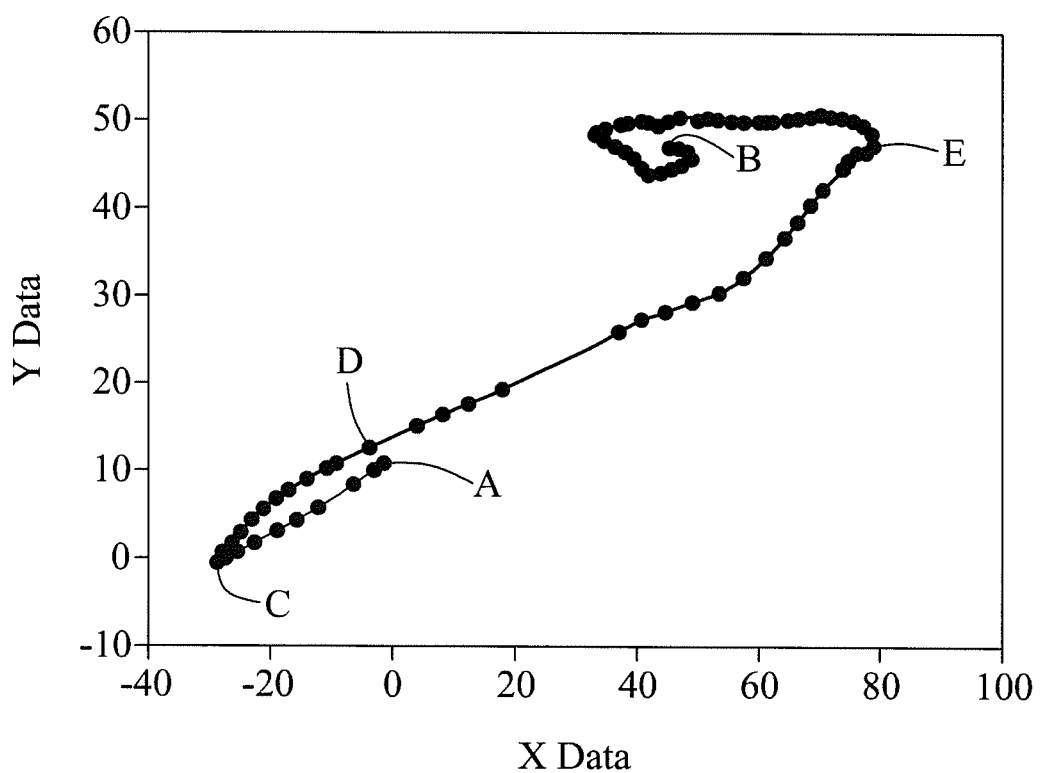
FIG. 3 is a diagram exemplifying an embodiment of a CoP trajectory.

The processor 122 of the electronic device 120 is configured to receive the sense signals from the respective sensors (114a-114d), and to execute an application program to generate CoP data associated with a CoP trajectory based on the sense signals received from the respective sensors (114a-114d), where the CoP trajectory indicates displacements of a CoP of the subject. To be more specific, the displacements of the CoP of the subject are associated with variations of the sense signals received from the respective sensors (114a-114d), and constitute the CoP trajectory, an example of which is shown in FIG. 3. In addition, the CoP data are stored in the memory 124.

FIG. 3 exemplifies the CoP trajectory obtained by the embodiment of the CoP based control system 100. Each point in FIG. 3 represents a location of the CoP determined based on the sense signals received from the respective sensors (114a-114d) at a corresponding time instance. Every two adjacent points corresponding to two successive time instances a unit time apart define a corresponding displacement of the CoP of the subject. Point A is a starting point of the CoP trajectory and is located at coordinates of approximately (0, 10), wherein the former coordinate is a horizontal coordinate of the CoP and the latter coordinate is a vertical coordinate of the CoP. Point B at coordinates of around (44, 47) is an end point of the CoP trajectory. Points C, D and E at coordinates of around (−30, −2), (−2, 12) and (78, 47), respectively, are intermediate points of the CoP trajectory. Point C is a possible turning point. Point D is an arbitrary point selected on the CoP trajectory for explanatory purposes. Point E is a point selected from neighbors of the end point (i.e., the point B), but selection of this point is not limited to what is disclosed herein. For example, a point succeeding the possible turning point and having the greatest displacement from the possible turning point along a direction from Point A to Point D may be selected. That is to say, the displacements (or a progressive shifting) of the CoP of the subject can be illustrated by the CoP trajectory depicting movement from point A, through points C, D, and E, and finally arriving at point B. It is worth noting that a movement of the CoP from point A, through points C and D, to point E corresponds to a process of a shift in a center of mass of the subject, and a segment between points E and B corresponds to a process in which the subject is trying to maintain balance.

In this embodiment, the processor 122 of the electronic device 120 is further configured to make a determination as to whether a turning point exists in the CoP trajectory so as to determine whether anticipatory postural adjustment (APA) exists (or occurs) in the subject. The existence of a turning point suggests that APA exists in the subject for posture control. For example, a turning point C exists in the CoP trajectory of the subject as shown in FIG. 3, while no similar turning point can be found in a CoP trajectory of a patient with Parkinson's disease (PD) because APA does not exist in the patient with PD when he/she controls his/her posture. In this way, the processor 122 determines that APA exists in the subject when it is determined that a turning point exists in the CoP trajectory.

It is worth noting that APA is a learnable ability that exists in a person in postural control so as to assist in voluntary movement, maintain balance (equilibrium) and reduce postural interference. By means of determining whether APA exists in the subject, it can be determined in at least one embodiment of this disclosure whether a compensatory movement exists (or occurs) in the subject for posture control. That is to say, the fact that APA does not exist in the subject indicates that a compensatory movement exists in the subject instead. When it is determined that a compensatory movement exists in the subject, it can be determined in said at least one embodiment of this disclosure that body movements performed by the subject for training purposes during the rehabilitation are incorrect. For example, APA is expected to exist in the subject when the subject shifts his/her center of mass from one leg to the other leg, but the subject actually shifts the center of mass by adopting a compensatory movement (e.g., bending his/her body or stretching his/her arm). Therefore, the CoP based control system 100 in said one embodiment of this disclosure determines that the subject's body movement is inappropriate for the purposes of rehabilitation based on the fact that APA does not exist in the subject. Moreover, depending on whether APA exists in the subject, said at least one embodiment of this disclosure can generate signals for further utilization, such as to provide notification to the subject or further instructions to the subject.

Specifically speaking, the determination as to whether a turning point exists in the CoP trajectory is made based on one of following factors or any combination thereof. The factors include, but are not limited to, a degree of an included angle between any adjacent two of the displacements of the CoP, a magnitude of (i.e., a distance corresponding to) one of the displacements of the CoP preceding a possible turning point on the CoP trajectory, and a ratio between magnitudes of two of the displacements of the CoP respectively preceding and succeeding a possible turning point (e.g., one of the two displacements may be defined by the possible turning point and a preceding adjacent point, and the other of the two displacements may be defined by the possible turning point and a succeeding adjacent point). For example, a possible turning point on the CoP trajectory is not determined to be a genuine turning point when a magnitude of a displacement of the CoP preceding the possible turning point is smaller than a predefined threshold. In practice, different weights can be assigned to the aforementioned factors so as to raise the truthfulness of the determination as to whether a turning point exists in the CoP trajectory.

In one embodiment, when it is determined by the processor 122 of the electronic device 120 that the ratio between magnitudes of two of the displacements of the CoP preceding and succeeding a possible turning point is greater than a preset ratio, such as 0.15, the processor 122 of the electronic device 120 determines that a turning point exists in the CoP trajectory, and that APA exists in the subject.

In one embodiment, when it is determined by the processor 122 of the electronic device 120 that the included angle between any adjacent two of the displacements of the CoP is less than 15 degrees and that the magnitude of one of the two displacements of the CoP preceding a possible turning point on the CoP trajectory is greater than 5 centimeters, the processor 122 of the electronic device 120 determines that a turning point exists in the CoP trajectory, and that APA exists in the subject.

In one embodiment, when it is determined by the processor 122 of the electronic device 120 that the included angle between any adjacent two of the displacements of the CoP is less than 30 degrees and that the magnitude of one of the two displacements of the CoP preceding a possible turning point on the CoP trajectory is greater than 10 centimeters, the processor 122 of the electronic device 120 determines that a turning point exists in the CoP trajectory, and that APA exists in the subject.

In one embodiment, when it is determined by the processor 122 of the electronic device 120 that the included angle between any adjacent two of the displacements of the CoP is less than 15 degrees and that the ratio between magnitudes of said two of the displacements of the CoP preceding and succeeding a possible turning point is greater than 0.05, the processor 122 of the electronic device 120 determines that a turning point exists in the CoP trajectory, and that APA exists in the subject.

In one embodiment, when it is determined by the processor 122 of the electronic device 120 that the included angle between any adjacent two of the displacements of the CoP is less than 30 degrees and that the ratio between magnitudes of said two of the displacements of the CoP preceding and succeeding a possible turning point is greater than 0.10, the processor 122 of the electronic device 120 determines that a turning point exists in the CoP trajectory, and that APA exists in the subject.

In another embodiment, a displacement may be defined by any two points on the CoP trajectory, e.g., by points A and C.

Referring to FIG. 3 again, a segment of the CoP trajectory from point A through point C to point E contains the turning point C. A vector from point A to point C (referred to as a vector AC hereinafter) is roughly opposite to a vector from point C to point E (referred to as a vector CE hereinafter) in direction. The included angle formed by a segment between points A and C (referred to as a segment AC) and a segment between points C and E (referred to as a segment CE) lies in the range of between 0 and 45 degrees. Lengths of the vector AC and the vector CE are respectively 31 centimeters and 117 centimeters, i.e., the length of the vector AC is one fourth of the length of the vector CE. Therefore, based on one of the factors mentioned above, the processor 122 of the electronic device 120 determines that a turning point exists in the CoP trajectory, and that APA exists in the subject. In other words, the subject corresponding to the CoP trajectory as shown in FIG. 3 is determined by the CoP based control system as performing expected body movements to achieve a shift of the center of mass.

Referring back to FIG. 1, the processor 122 of the electronic device 120 is further configured to generate an indication signal based on a result of the determination as to whether a turning point exists in the CoP trajectory, where the indication signal indicates whether or not APA exists in the subject. The output port 126 of the electronic device 120 is configured to output the indication signal. Specifically, when it is made in the determination that a turning point exists in the CoP trajectory, the indication signal is generated to indicate that APA exists in the subject. Contrastingly, when it is made in the determination that a turning point does not exist in the CoP trajectory, the indication signal is generated to indicate that APA does not exist in the subject.

The processor 122 of the electronic device 120 is further configured to execute the application program to generate a control signal based on a direction of one of the displacements of the CoP. The output port 126 of the electronic device 120 is further configured to output the control signal.

In one embodiment, the control signal is to be used for controlling movement of a virtual object, such that the virtual object moves as if it were controlled by a keyboard, a mouse, or any other input devices. Specifically speaking, the control signal is utilized to control a direction of the movement of the virtual object, e.g., up, down, left, right, such that the direction of the movement corresponds to said one of the displacements of the CoP of the subject. In other words, content of (or instruction conveyed by) a control signal, e.g., to move up, is determined based on the direction of the corresponding displacement of the CoP.

In one embodiment, a frequency of generation of the control signal is based on whether APA exists in the subject. When it is determined that the APA exists in the subject, the displacement of the CoP influences the frequency of generation of the control signal. A greater displacement of the CoP results in a higher frequency of generation of the control signal. On the other hand, when it is determined that the APA does not exist in the subject, i.e., a compensatory movement exists in the subject, no control signal is generated.

In one embodiment, the electronic device 120 is further configured to determine an operation mode (e.g., the aforementioned embodiment where the generation of the control signal is based on a result of the determination as to whether APA exists in the subject) in which the CoP based control system 100 is to operate based on whether APA exists in the subject. For example, in a scenario where the CoP based control system 100 is used to check whether APA exists in the subject when the subject is following instructions generated by a computer program of rehabilitation to perform corresponding body movements on the platform 110, the CoP based control system 100 resets and restarts the computer program of rehabilitation when it is determined by the CoP based control system 100 that APA does not exist in the subject. The computer program of rehabilitation may be executed by either the electronic device 120 or an external computer that is connected electrically to the electronic device 120.

Figure 4:
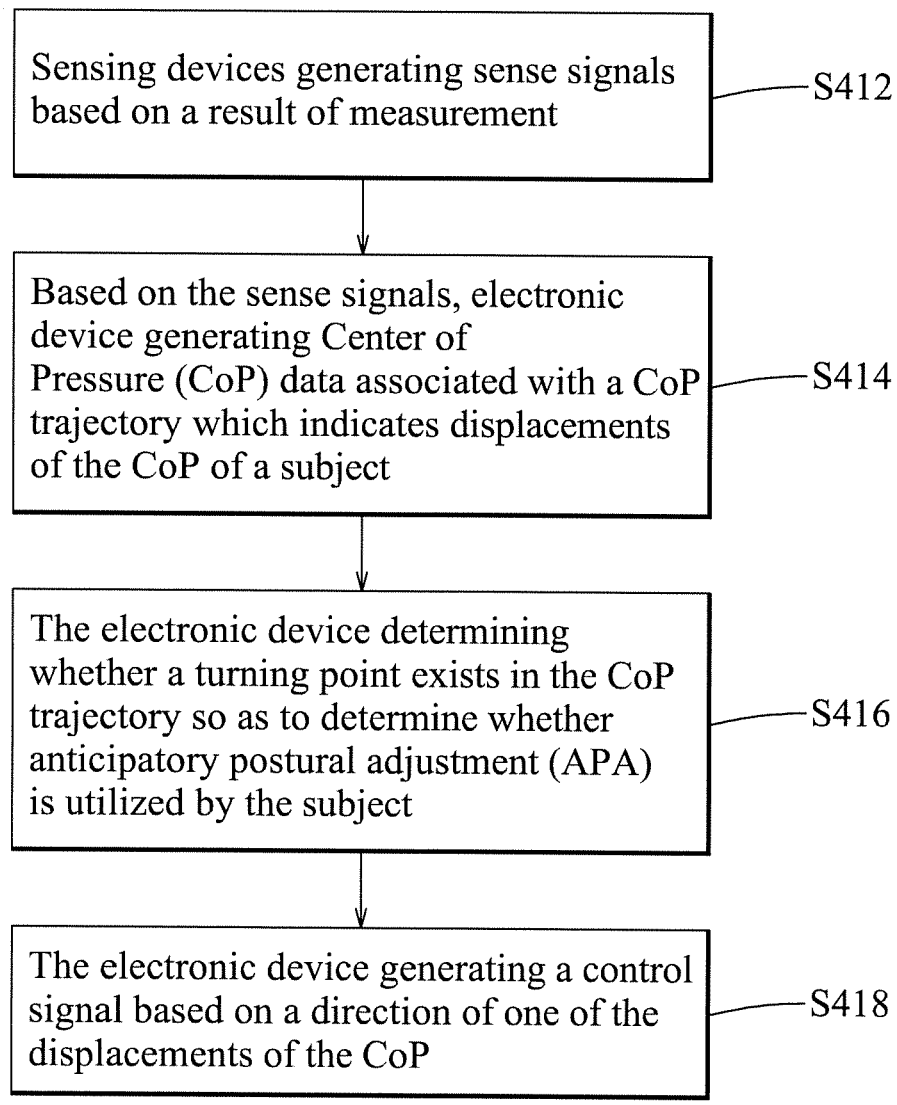
FIG. 4 is a flow chart illustrating an embodiment of a CoP based control method according to the disclosure.

Referring to FIG. 4, an embodiment of a CoP based control method is illustrated. The CoP based control method is to be implemented by the CoP based control system 100 previously mentioned and shown in FIG. 1. The CoP based control method includes steps S412, S414, S416 and S418 described in the following.

In step S412, each of the sensors (114*a*-114*d*) of the CoP based control system 100 makes continuous measurement of force exerted thereon by the subject, and generates the sense signal based on the result of the measurement. The electronic device 120 of the CoP based control system 100 receives the sense signals from the respective sensors (114*a*-114*d*).

In step S414, the electronic device 120 of the CoP based control system 100 generates, based on the sense signals received from the respective sensors (114*a*-114*d*), CoP data associated with the CoP trajectory which indicates displacements of the CoP of the subject.

In step S416, the electronic device 120 of the CoP based control system 100 makes a determination as to whether a turning point exists in the CoP trajectory so as to determine whether APA exists in the subject. Based on the result of the determination, the electronic device 120 of the CoP based control system 100 generates the indication signal which indicates whether or not APA exists in the subject. In this embodiment, the determination as to whether a turning point exists in the CoP trajectory is made based on at least one of an included angle between any adjacent two of the displacements of the CoP, a magnitude of one of the displacements of the CoP preceding a possible turning point on the CoP trajectory, or a ratio between magnitudes of two of the displacements of the CoP preceding and succeeding the possible turning point.

In step S418, the electronic device 120 of the CoP based control system 100 generates the control signal based on a direction of one of the displacements of the CoP. The control signal can be further defined so as to serve as an input signal for different applications.

In one embodiment, the CoP based control method further includes a step where the electronic device 120 determines an operation mode in which the CoP based control system 100 is to operate based on whether APA exists in the subject.

Another embodiment of the CoP based control method is similar to the embodiment of the CoP based control method previously mentioned, but is different in the following steps. The electronic device 120 of the CoP based control system 100 makes a determination as to whether a turning point exists in the CoP trajectory so as to determine whether a compensatory movement exists in the subject, and based on a result of the determination, generates an indication signal which indicates whether or not a compensatory movement exists in the subject. In such embodiment, the determination as to whether a turning point exists in the CoP trajectory for determining whether compensatory movement exists in the subject is made based on at least one of an included angle between any adjacent two of the displacements of the CoP, a magnitude of one of the displacements of the CoP preceding a possible turning point on the CoP trajectory, or a ratio between magnitudes of two of the displacements of the CoP preceding and succeeding the possible turning point. Additionally, the electronic device 120 of the CoP based control system 100 determines an operation mode in which the CoP based control system 100 is to operate based on whether a compensatory movement exists in the subject.

In one embodiment, the processor 122 of the electronic device 120 generates the control signal to control movement of a virtual object, which serves as an avatar of the subject in the computer program of rehabilitation. For example, the computer program of rehabilitation may be implemented as a video game which includes a plurality of tasks to be performed by the subject. For instance, one task may request the subject to control, via moving his/her body to shift his/her center of mass while standing on the platform 110, the virtual object to move along a route and/or to avoid obstacles in the video game. According to the displacements of the CoP of the subject, the virtual object can be controlled correspondingly to step forward, backward, to the left, to the right, to the left and forward, to the left and backward, to the right and forward, or to the right and backward in the video game. In one embodiment, the processor 122 of the electronic device 120 may be implemented to determine, based on the CoP data generated thereby, whether the subject has shifted his/her center of mass within a time period having a preset duration (e.g., 3 seconds) so as to decide if the subject has successfully manipulated his/her body movement for generation of a corresponding control signal. For one of the tasks, the subject may be requested to shift his/her center of mass so as to enable the CoP based control system 100 to successively generate control signals for controlling the virtual object to move along the route and to avoid the obstacles within a time period having a first predetermined duration. Said one of the tasks is determined to have not been completed when the subject fails to control the virtual object to accomplish the aforementioned actions (i.e., to move along the route and to avoid the obstacles) within the time period having the first predetermined duration. In one embodiment, the processor 122 of the electronic device 120 may be implemented to determine whether the subject correctly control his/her center of mass to accomplish a series of actions (e.g., stepping forward immediately followed by stepping to the left) within a time period having a second predetermined duration (e.g., 10 seconds) such that the CoP trajectory correspondingly obtained matches a predetermined trajectory. In this way, the subject may be informed of whether an adjustment is needed while shifting the center of mass.

In one embodiment, when it is determined by the processor 122 of the electronic device 120 that APA does not exist in the subject, the processor 122 of the electronic device 120 ceases to generate the control signal, and generates the indication signal that is to be displayed by a display of the electronic device 120 or an external display, so that the subject can be notified to adjust the way of controlling movement of the virtual object so that APA can occur in the subject.

Going back to the previously mentioned computer program of rehabilitation, for one of the displacements of the CoP of the subject, a corresponding moving distance of the virtual object in the computer program of rehabilitation is proportional to the total number of outputs of the control signal that is outputted by the CoP based control system 100 for said one displacement, where each control signal corresponds to a unit amount of movement of the virtual object, and the outputs of the control signal (totaling to the total number) all result from said one displacement. In other words, the content of the control signal (e.g., to move to the left) is determined based on the direction of the corresponding displacement, and the number of times this control signal is outputted by the output port 126 (corresponding to, e.g., to move to the left by how many unit distances) is determined based on the magnitude of the corresponding displacement. That is to say, the greater the magnitude of said one displacement of the CoP, the greater the total number of outputs of the control signal, and the greater the moving distance of the virtual object.

In one embodiment, the electronic device 120 is configured to, when it is determined that APA does not exist in the subject, adjust at least one threshold value that is stored in the memory 124 and that is associated with generation of the control signal(s).

Moreover, the electronic device 120 is configured to adjust output(s) of the control signal based on a relationship between said at least one threshold value and a magnitude of said one of the displacements of the CoP. For example, said at least one threshold value may be implemented to include an upper threshold and a lower threshold. The processor 122 executes a configuration program so as to adjust in advance a value of the upper threshold and a value of the lower threshold according to a preliminary usage of the CoP based control system 100 by the subject. To reflect the magnitude of said one of the displacements of the CoP on the movement of the virtual object in the computer program of rehabilitation, the control signal may be outputted in the following manner. The processor 122 disables the output port 126 so that the output port 126 does not output the control signal when the processor 122 determines that the magnitude of said one of the displacements of the CoP is not greater than the lower threshold. When the processor 122 determines that the magnitude of said one of the displacements of the CoP is greater than the lower threshold, the processor 122 enables the output port 126 to output the control signal. When the processor 122 determines that the magnitude of said one of the displacements of the CoP is greater than the lower threshold and is proximate to but lower than the upper threshold, the processor 122 increases a frequency of outputting of the control signal so as to accelerate the movement of the virtual object in the computer program of rehabilitation. Therefore, the greater the magnitude of the displacement of CoP, the faster the virtual object moves and the longer distance the movement of the virtual object.

In one embodiment, the processor 122 may be implemented to, when it is determined that the magnitude of said one of the displacements of the CoP is greater than the lower threshold and is proximate to but lower than the upper threshold (i.e., when the subject intends to accelerate the movement of the virtual object for accomplishing the task in a shorter time), reduce the first predetermined duration in the computer program of rehabilitation so as to provide a higher degree of challenge to the subject. In this way, effect of rehabilitation may be improved.

In one embodiment, the processor 122 may be implemented to increase difficulty of the task in the computer program of rehabilitation. For example, the processor 122 may increase the difficulty of a current task by increasing the lower threshold when the processor 122 determines that the subject has performed well in a previous task, so that the subject needs to put more effort in the current task, i.e., to increase a degree of body movement to result in displacements of the CoP of the subject having greater magnitudes, for achieving the same amount of movement of the virtual object in the current task as that in the previous task. In this way, the subject may be more willing to engage in the computer program of rehabilitation.

It is worth to note that the control signal of the CoP based control system 100 can be utilized in different applications, e.g., to serve as an input signal to a general personal computer (PC) for regular operations on the PC, and is not limited to being used in rehabilitation purposes. Therefore, controlling other devices by displacements of the CoP can be realized. Moreover, since the control signal of the CoP based control system 100 is generated according to protocols regarding general input devices or human interface devices, the control signal can be conveniently exploited by computer programmers, facilitating development of products which are compatible with the CoP based control system 100.

In summary, the CoP based control system 100 generates CoP data based on measurements of the sensing device 112, determines whether a turning point exists in the CoP trajectory established based on the CoP data so as to determine whether APA exists in the subject, generates the indication signal based on the result of the determination, and generates the control signal based on the direction of one displacement of the CoP. The control signal may be utilized to control movement of the virtual object in the computer program of rehabilitation so as to facilitate the process of rehabilitation. Adjusting said at least one threshold value for controlling the generation of the control signal is beneficial for development of more interesting computer programs of rehabilitation so as to enhance involvement of the subject in the process of rehabilitation, and thereby the effect of rehabilitation may be improved.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A center of pressure (CoP) based control system, comprising:

a sensing device including a plurality of sensors each of which is configured to generate a sense signal based on a result of measurement made by the sensor; and a processor electrically coupled to said sensing device, and configured to receive the sense signals from the respective sensors, to generate, based on the sense signals received from the respective sensors, CoP data associated with a CoP trajectory which indicates displacements of a CoP in a spatial coordinate system defining physical space, to make a determination based on a characteristic of the CoP trajectory, as to whether a turning point exists in the CoP trajectory and to thereby generate an indication signal, and to generate a control signal based on the indication signal and a direction of one of the displacements of the CoP, wherein when it is determined that the turning point does not exist in the CoP trajectory, the indication signal indicates that an anticipatory postural adjustment (APA) does not occur in a subject and that a compensatory movement occurs in the subject, wherein when it is determined that the turning point exists in the CoP trajectory, the indication signal indicates that the APA occurs in the subject and that the compensatory movement does not occur in the subject, wherein the control signal is used as an input signal to an electronic device for controlling operation of the electronic device, wherein the characteristic of the CoP trajectory is at least one of: an included angle between any adjacent two of the displacements; a magnitude of one of the displacements; and a ratio between magnitudes of two of the displacements, wherein the indication signal indicates that the compensatory movement does not occur in the subject when the included angle is less than a predetermined degree, wherein said processor is configured to generate the control signal only when the indication signal indicates that the APA occurs in the subject, wherein said processor is further configured to, when it is determined that the magnitude of said one of the displacements of the CoP is greater than a lower threshold and is proximate to but lower than an upper threshold, increase a frequency of outputting of the control signal, and wherein said processor is further configured to, when it is determined that the subject needs to put more effort, increase the lower threshold so that the subject is required to increase a degree of body movement to result in displacements of the CoP of the subject having greater magnitudes.

2. The control system as claimed in claim 1, wherein the indication signal indicates that the compensatory movement does not occur in the subject when the magnitude of one of the displacements is greater than a predetermined length.

3. The control system as claimed in claim 1, wherein the indication signal indicates that the compensatory movement does not occur in the subject when the ratio between magnitudes of two of the displacements is greater than a predetermined ratio.

4. The CoP based control system as claimed in claim 1, wherein said sensing device is disposed on two platforms for supporting the subject.

5. The CoP based control system as claimed in claim 1, wherein said processor is configured to determine an operation mode in which the CoP based control system is to operate based on whether the compensatory movement occurs in the subject.

6. The CoP based control system as claimed in claim 1, wherein the control signal is to be used for controlling movement of a virtual object.

7. A center of pressure (CoP) based control method, to be implemented by a CoP based control system, said method comprising:

by each of a plurality of sensors of the CoP based control system, generating a sense signal based on a result of measurement made by the sensor;

by a processor of the CoP based control system, receiving the sense signals from the respective sensors;

by the processor of the CoP based control system, generating, based on the sense signals received from the respective sensors, CoP data associated with a CoP trajectory which indicates displacements of a CoP in a spatial coordinate system defining physical space;

by the processor of the CoP based control system, making a determination based on a characteristic of the CoP trajectory, as to whether a turning point exists in the CoP trajectory and thereby generating an indication signal; and by the processor of the CoP based control system, generating a control signal based on the indication signal and a direction of one of the displacements of the CoP, wherein when it is determined that the turning point does not exist in the CoP trajectory, the indication signal indicates that an anticipatory postural adjustment (APA) does not occur in a subject and that a compensatory movement occurs in the subject, wherein when it is determined that the turning point exists in the CoP trajectory, the indication signal indicates that the APA occurs in the subject and that the compensatory movement does not occur in the subject, wherein the control signal is used as an input signal to an electronic device for controlling operation of the electronic device, wherein the characteristic of the CoP trajectory is at least one of: an included angle between any adjacent two of the displacements; a magnitude of one of the displacements; and a ratio between magnitudes of two of the displacements, and wherein the indication signal indicates that the compensatory movement does not occur in the subject when the included angle is less than a predetermined degree, wherein the control signal is generated only when the indication signal indicates that the APA occurs in the subject, said method further comprising:

increasing, when it is determined that the magnitude of said one of the displacements of the CoP is greater than a lower threshold and is proximate to but lower than an upper threshold, a frequency of outputting of the control signal; and increasing, when it is determined that the subject needs to put more effort, the lower threshold so that the subject is required to increase a degree of body movement to result in displacements of the CoP of the subject having greater magnitudes.

8. The CoP based control method as claimed in claim 7, wherein the indication signal indicates that the compensatory movement does not occur in the subject when the magnitude of one of the displacements is greater than a predetermined length.

9. The CoP based control method as claimed in claim 7, wherein the indication signal indicates that the compensatory movement does not occur in the subject when the ratio between magnitudes of two of the displacements is greater than a predetermined ratio.

10. The CoP based control method as claimed in claim 7, further comprising determining an operation mode in which the CoP based control system is to operate based on the indication signal.

11. The CoP based control method as claimed in claim 7, wherein the sensors are disposed on two platforms for supporting the subject.

12. A center of pressure (CoP) based control method, to be implemented by a CoP based control system, the CoP based control system including a processor and a plurality of sensors, said method comprising:

generating, by each of the sensors, a sense signal based on a result of measurement made by the sensor;

receiving, by the processor, the sense signals from the respective sensors;

generating, by the processor based on the sense signals received from the respective sensors, CoP data associated with a CoP trajectory which indicates displacements of a CoP in a spatial coordinate system defining physical space; and by the processor, making a determination, based on a characteristic of the CoP trajectory, as to whether a turning point exists in the CoP trajectory and thereby generating an indication signal, and generating a control signal based on the indication signal and a direction of one of the displacements of the CoP;

wherein when it is determined that the turning point exists in the CoP trajectory, the indication signal indicates that an anticipatory postural adjustment (APA) exists in a subject, wherein when it is determined that the turning point does not exist in the CoP trajectory, the indication signal indicates that the APA does not exist in the subject, wherein the control signal is used as an input signal to an electronic device for controlling operation of the electronic device, wherein the characteristic of the CoP trajectory is at least one of: an included angle between any adjacent two of the displacements, a magnitude of one of the displacements, and a ratio between magnitudes of two of the displacements, wherein the control signal is generated only when the indication signal indicates that the APA exists in the subject, said method further comprising:

increasing, when it is determined that the magnitude of said one of the displacements of the CoP is greater than a lower threshold and is proximate to but lower than an upper threshold, a frequency of outputting of the control signal; and increasing, when it is determined that the subject needs to put more effort, the lower threshold so that the subject is required to increase a degree of body movement to result in displacements of the CoP of the subject having greater magnitudes.

* * * * *